US00PP18416P2

(12) United States Plant Patent
Berry

(10) Patent No.: US PP18,416 P2
(45) Date of Patent: Jan. 15, 2008

(54) ***AZALEA* PLANT NAMED 'MOOTUM'**

(50) Latin Name: *Rhododendron hybrid*
Varietal Denomination: Mootum

(76) Inventor: James Bryan Berry, 25075 Austin Rd., Daphne, AL (US) 32526

( * ) Notice: Subject to any disclaimer, the term of this patent is extended or adjusted under 35 U.S.C. 154(b) by 18 days.

(21) Appl. No.: 11/297,143

(22) Filed: Dec. 8, 2005

(51) Int. Cl.
*A01H 5/00* (2006.01)

(52) U.S. Cl. ..... Plt./238

(58) Field of Classification Search ..... Plt./238
See application file for complete search history.

*Primary Examiner*—Kent Bell
*Assistant Examiner*—June Hwu

(57) ABSTRACT

A new and distinct variety of *Azalea* found as a mutant sport of *Azalea* 'Conleo'. The new variety possesses a unique blooming time and is superior in development. An upright, dense, globose shaped plant with attractive, ruffled, large semi-double white flowers.

1 Drawing Sheet

Latin name: *Rhododendron* hybrid 'Mootum'.
Variety denomination: 'Mootum'.

BACKGROUND OF THE INVENTION

The present invention relates to a new and distinct variety of evergreen *azalea* of the genus *Rhododendron* and a member of the Ericaceae family. This new *azalea* variety, hereinafter referred to as 'Mootum', was discovered by James Bryan Berry in 2001 in Loxley, Ala. 'Mootum' was discovered as a naturally occurring sport mutation of the *Azalea* plant named 'Conleo', U.S. Plant Pat. No. 11,640. The value of this new cultivar lies in its unique blooming period, bloom color, bloom form, bloom size, and growth habit.

Asexual propagation of the new plant by cuttings has been under Mr. Berry's direction in Loxley, Ala. Several generations of the new plant have been evaluated and the distinctive characteristics of the plant have remained stable. The plant cannot be reproduced true from seed.

BRIEF DESCRIPTION OF ILLUSTRATION

This new *Azalea* Hybrid variety is illustrated by the accompanying photographic prints in which:

1. FIG. 1 is a close-up showing flower and foliage of the new cultivar 'Mootum'.

The colors shown are as true as is reasonably possible to obtain by conventional photographic procedures. The colors of the various plant parts are defined with reference to The Royal Horticultural Society Colour Chart (R.H.S.C.C.). Description of colors in ordinary terms are presented where appropriate for clarity in meaning. Colors in the photographs may appear different than actual colors due to light reflectance. Color values cited in the Botanical Description of the Plant accurately describe the actual colors of the new *Azalea*.

DETAILED BOTANICAL DESCRIPTION OF THE PLANT

The following is a detailed description of the new variety of *Azalea* based on my observations made of plants grown in wholesale commercial production practices, in greenhouses, and in established landscape plantings in Loxley, Ala.

Distinctive Characteristics:

TABLE 1

| Characteristic | 'Mootum' | 'Conleo' |
|---|---|---|
| Height (Mature) | 5-6' | 5-6' |
| Width (Mature) | 5-6' | 5-6' |
| Flower Size | 2½-3" | 2½-3" |
| Flower Form | Semi-double | Semi-double |
| Flower Color | 155D | 44D |
| Throat Color | 4D | 44D |
| Flowers per Terminal | 2-4 | 2-4 |
| Bloom Period | April | April |
| Bloom Period | Mid-July > Frost | Mid-July > Frost |
| Petal Number | 10-15 | 10-15 |
| Hardy Zone | 7 | 7 |
| Stamen Number | 0-5 | 0-5 |
| Stamen Type | Some Petaloid | Some Petaloid |

Classification:

*Botanic.*—*Rhododendron* hybrid 'Mootum'.

*Form.*—Upright, dense, and rounded.

*Height.*—5'.

*Width.*—4'.

*Growth habit.*—Upright, dense and globose. Fast growth rate under normal fertilization and moisture conditions.

*Growth rate.*—In a period of six years from a rooted cutting the plant reaches a height of 3 feet and a spread of 4 feet. The growth rate is normally about 10 to 12" per year; the plant reaches an approximate height of 5' at maturity while maintaining a dense habit due to the abundant branch development.

*Foliage.*—Alternate, simple, evergreen, pubescent, elliptic, and varying in size from 1½" to 1⅞" long and ⅝" to 13/16" wide. The margins are entire, with a petiole 3/16" to 5/16" long. Midveins and laterals are impressed on the upper leaf surface and prominent on the underside. The base of the leaf is cuneate to attenuate and the apex is acute to mucronate. The upper surface of the immature leaves are dull, pubescent, and are RHSCC Yellow-Green Group 144A and the underside is RHSCC Yellow-Green Group 146D, pubescent, and the matte. The upper surface of the mature leaves are RHSCC Yellow-Green Group 146A, dull and slightly pubescent and the underside is RHSCC Yellow-Green Group 146C, matte, and pubescent. The immature petioles, mid-ribs and veins are RHSCC Yellow-Green Group 146C. New growth is pubescent. These hairs are initially soft and white and cover both sides of the leaf with a higher concentration on the petioles and veins. They are slightly curled, flat, and range in length from 1/32" to 1/8". As the growth matures much of the leaf pubescence is lost; however, the stems, petioles, and leaf veins retain this pubescence which becomes more setaceous and darker in color (RHSCC Brown Group 200A) through the growing season.

In 2005, the date of initial spring growth was March 15, in Loxley, Ala. After the initial spring flush there was almost continuous growth until that fall ending October 20, also in Loxley, Ala. When grown in full sun, the internode length of this plant is 3/16" to 1/2"; when grown in light shade the internode length is 3/8" to 5/8". As would be expected a plant grown in shade results in a taller, less dense plant with larger leaves.

The average length of terminal growth of the initial spring flush is about 6" for a plant in full sun and about 8" when grown in shade. This growth should not be trimmed since it will produce flowers starting in mid July. As the plant continues to grow through the summer and fall more flower buds are produced, which mature and bloom until frost. This remaining growth produces about 5" to 6" of height. As cool weather approaches, some of the flower buds become dormant. These buds bloom in April of the next year.

*Stems.*—The young stems are RHSCC Yellow-Green Group 146C and densely clothed with spreading white glandular hairs. During the second growing season they become RHSCC Greyed-Green Group 197B, glabrous and rugose. The pith is solid and uniform. Young and older stems are densely branched. The mature stem is RHSCC Grey-Brown Group 199A in color.

*Buds.*—Tight buds at 1/2" are ovate and acuminate RHSCC Yellow-Green Group 146D with a hairy pubescence Brown Group 200A. The buds are borne in clusters of 2 to 4, and are sheathed by a pair of modified leaf bracts which are from 1/4" to 1/2" long, persistent, and RHSCC Yellow-Green Group 147A. The pedicel is 3/8" to 1/2" long, pubescent, and RHSCC Red Group 53C. The calyx is 1/8" to 1/4" long, RHSCC Yellow-Green Group 144B, funnel shaped, persistent, and pubescent. The five imbricated sepals are lanceolate and joined at the base to form a cup. As the buds swell the bud sheath matures to a RHSCC Greyed-Orange Group 165A, falls off, and reveals the flower color RHSCC White Group 155D.

*Flowers.*—Perfect, semi-double, upper surface of throat and flecking is RHSCC Yellow Group 4D Upper Surface petal color is RHSCC White Group 155D Lower surface petal is RHSCC White Group 155C. Petals are 1 1/4" long and 9/16" wide. Each petal has a stripe from throat to tip (one stripe per flower) that is RHSCC Red/Purple Group 62D. Glabrous, openly funnel shaped flowers are 2 1/2" to 3" wide by 2" to 2 1/4" long, borne on current season's growth, non-fragrant; they last on the plant in the garden 5 to 6 days. There are five true petals which are fused at the base, elliptic to obovate, and have wavy margins. There are 0 to 5 non-petaloid stamen which are 1/4" to 1" long. The filaments and the anthers are both colored RHSCC Yellow Green Group 145D and the pollen matures to RHSCC Yellow Group 11B. The 5 to 10 petaloid stamen are from 3/4" to 2" long and odd shaped. The petaloid stamen's color is RHSCC White Group 155C. The uppermost petaloid stamen are dotted. The dots are colored RHSCC White Group 155B. The pistil is single, non-petaloid, 3/4" to 1 1/2" long and the ovary is densely glandular-setose and has five locules. The pubescent peduncle is 5 mm long and it's color is RHSCC Yellow-Green Group 149C. Fruit was not observed. There is a 2 to 3 week flowering period in April in Loxley, Ala. Flowering resumes in mid July as the new buds mature and continues until frost which can be as late as November or December in Loxley, Ala. *Azaleas* blooming at this time of year attract butterflies in profusion.

*Culture.*—Grows well in a wide range of conditions, tolerates sun to shade. Prefers a moist, well-drained soil that is rich in organic matter. Responds well to mulching and medium applications of fertilizer; prefers ph 5.0 to 5.5. Very little pruning is needed; adaptable to container and above ground planters; makes a good foundation plant or informal hedge with excellent foliage and flower contrast. Ideal for coastal regions and warmer parts of Piedmont. Propagated with semi-hardwood cuttings in late spring through the summer.

Pests: Lace wing and spider mites can be a problem.

Other Data Provided

Comparison with Parent

All characteristics except flower bloom and throat color identical to *Azalea* 'Conleo', from which the sport mutant 'Mootum' originated.

SUMMARY OF THE INVENTION

The following are the most outstanding and distinguishing characteristics of this new cultivar when grown under normal horticultural practices in Loxley, Ala.

1. The unique spring, summer, and fall blooming.
2. A white and yellow flower. Throat and flecking is Yellow Group 4D, Petal color is White Group 155D, Stripe from throat to tip (one stripe per flower) Red/Purple Group 62D.
3. Large, semi-double flower with wavy petal margins. The flowers average 2 1/2" in diameter.
4. Easily propagated with semi-hardwood cuttings in late spring through the summer.
5. Fast growth rate under normal fertilization and moisture conditions.
6. Upright, dense and globose in nature.
7. Good specimen plant.
8. Desirable in planters.
9. Makes a very good hedge or screen.
10. Very good foundation plant for large buildings.
11. Does well as an understory plant in a woodland garden.
12. Hardy to Zone 7.
13. Attracts butterflies.

It is claimed:

1. A new and unique variety of *Azalea* plant named 'Mootum' as herein shown and described.

* * * * *

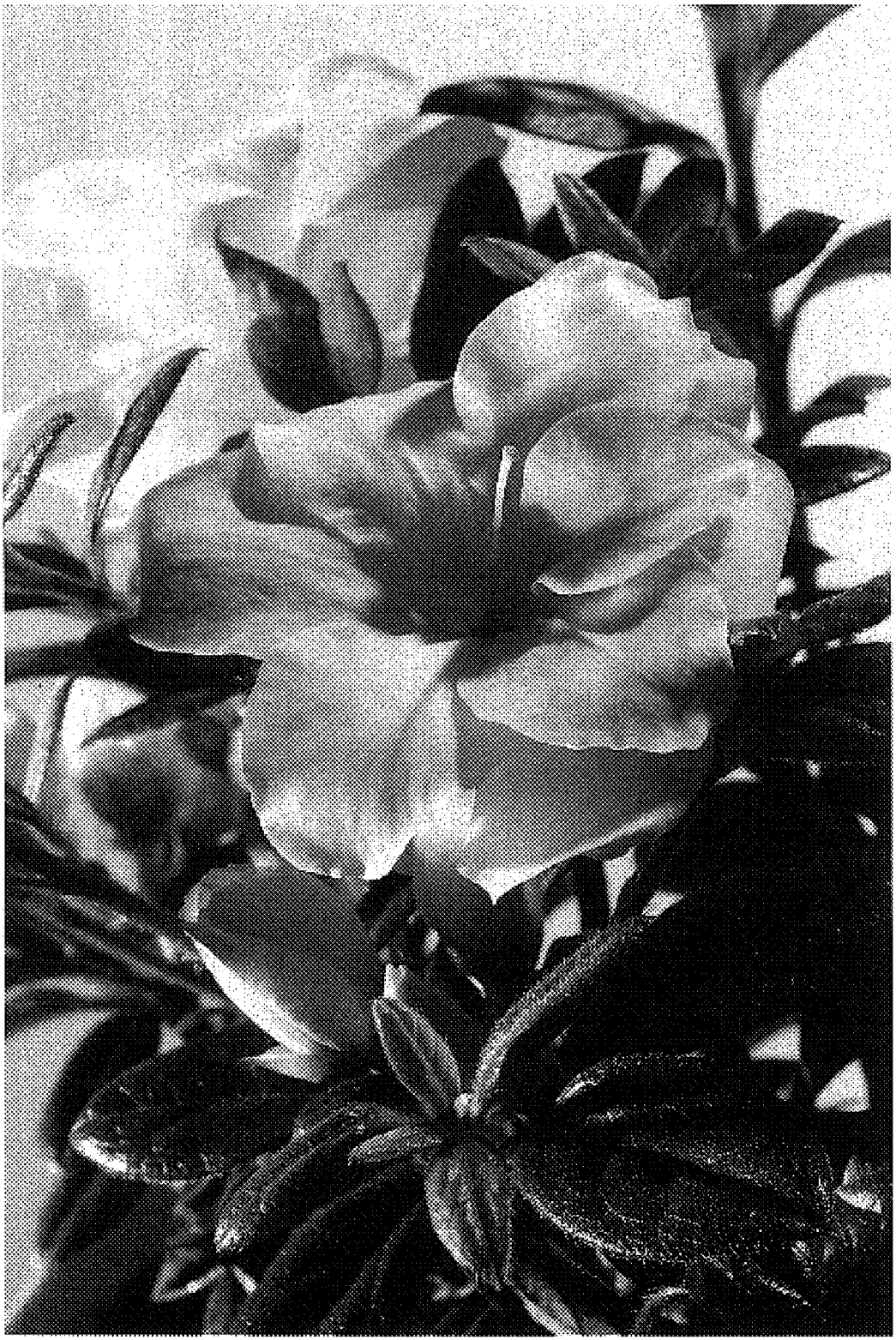
figure one

UNITED STATES PATENT AND TRADEMARK OFFICE
Certificate

Patent No. PP18,416 P2 Patented: January 15, 2008

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Amy Duck Thomas, Bokeelia, FL (US).

Signed and Sealed this Twentieth day of April 2010.

ANNE MARIE GRUNBERG
*Supervisory Patent Examiner*
Art Unit 1661